(12) United States Patent
Ganguli et al.

(10) Patent No.: US 8,546,002 B2
(45) Date of Patent: Oct. 1, 2013

(54) YEAST BIOFILM BASED FUEL CELL

(75) Inventors: Rahul Ganguli, Oak Park, CA (US);
Vivek Mehrotra, Simi Valley, CA (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 559 days.

(21) Appl. No.: 12/606,056

(22) Filed: Oct. 26, 2009

(65) Prior Publication Data

US 2011/0097605 A1     Apr. 28, 2011

(51) Int. Cl.
*H01M 8/16*     (2006.01)
*H01M 8/00*     (2006.01)

(52) U.S. Cl.
USPC .............................................. 429/2; 429/400

(58) Field of Classification Search
USPC ..................................................... 429/2, 400
See application file for complete search history.

(56) References Cited

U.S. PATENT DOCUMENTS

| | | | | |
|---|---|---|---|---|
| 3,331,705 | A * | 7/1967 | Davis et al. ........................ | 429/2 |
| 2003/0138674 | A1 * | 7/2003 | Zeikus et al. ...................... | 429/2 |
| 2004/0241528 | A1 * | 12/2004 | Chiao et al. ....................... | 429/43 |
| 2006/0254931 | A1 * | 11/2006 | Lin et al. ........................... | 205/775 |
| 2007/0059565 | A1 * | 3/2007 | Siu et al. ............................ | 429/2 |
| 2007/0259217 | A1 * | 11/2007 | Logan ................................ | 429/2 |

FOREIGN PATENT DOCUMENTS

WO     WO 2008057318 A1 *     5/2008

OTHER PUBLICATIONS

Logan et al. Environmental Science and Technology Sep. 1, 2006 pp. 5172-5180.*
Wikipedia (*E. coli* Wikipedia printed Feb. 25, 2012) {http://wikipedia.org/wiki/Eschenichia_coli}.*
Liu et al. (Environmental Science and Technology 2004 vol. 38 pp. 4040-4046).*
Park et al. (Biotechnology and Bioengineering 2003 vol. 81 No. 3 pp. 348-355).*
Ganguli et al Fuel Cells vol. 9 No. 1 pp. 44-52 Feb. 2009 Online Date Sep. 16, 2008 a.*
Kim et al Environmental Science and Technology vol. 41 2007 pp. 1004-1009.*
Dufty (EMR Labs Extraction of Sugar Blues, Chilton Book Co. Padnor PA (C) 1975 {http://www.quantumbalancing.com/news/sugar_blues.htm} and also in further view of Potter (Potter 1911 Proc. R Soc. London B vol. 84 pp. 260-276).*
Potter (Potter 1911 Proc. R Soc. London B vol. 84 pp. 260-276).*

(Continued)

*Primary Examiner* — Patrick Ryan
*Assistant Examiner* — Aaron Greso
(74) *Attorney, Agent, or Firm* — Glenn H. Lenzen; Husch Blackwell LLP

(57) ABSTRACT

A yeast biofilm microbial fuel cell has anode and cathode chambers, each containing an electrolyte medium, separated by a proton conducting membrane. A baker's yeast biofilm is induced to form on the anode under electrical poising. A method of making the MFC includes adding baker's yeast and yeast nutrient fuel source to the anode solution, connecting a resistor across the anode and cathode to enable current flow through the resistor for a selected time for poising the anode and formation of the anodic yeast biofilm, replacing the anode solution with a fresh quantity of yeast-free solution, adding fuel source to the solution, and continuing to run the MFC for a selected time under resistance. The steps of replacing the anode solution, adding fuel source and running the cell under load are repeated until the baker's yeast has formed a suitable anodic biofilm.

29 Claims, 3 Drawing Sheets

(56) References Cited

OTHER PUBLICATIONS

Bassir (West African Journal of Bio. Chem., 1962 vol. 6 No. 2 pp. 20-25).*

Park et al. Applied Microbiolgy and Biotechnology 2002 vol. 59 pp. 58-61.*

Shinji et al. (Nippon Kikai Gakkai Kankyo Kogaku Sogo Shinpojiumu Koen Ronbunshu vol. 16 pp. 424-427 2006 Abstract).*

* cited by examiner

YEAST BIOFILM BASED FUEL CELL

STATEMENT REGARDING FEDERALLY SPONSORED RESEARCH OR DEVELOPMENT

This invention was made with Government support under G.O. 71298 awarded by DARPA DSO. The Government has certain rights in this invention.

BACKGROUND OF THE INVENTION

The present disclosure is broadly concerned with microbial fuel cells. More particularly, it is concerned with a high power density yeast-catalyzed microbial fuel cell having a biofilm of baker's yeast cells adhered to the anode.

There is great interest is using microbial fuels cells (MFCs) to harvest energy from diverse natural feeds such as wastewater and ocean sediments. The high efficiency of conversion of biomass energy directly to electrical energy in such MFCs makes this a compelling approach to both large and small scale power generation. Dirty, untreated natural sugars could be used as fuel in MFCs catalyzed by inexpensive and self-renewing microbes. Abundant, widely available natural sugars such as raw tree sap could be used to provide an emergency power supply for sensors and other devices having low power requirements. However, thus far the amount of power generated by such MFCs per unit of volume is very low. In order to effectively use readily available natural feed sources such as plants as an interface for fuel cell power generation, the power density of such fuel cells must be increased substantially.

Yeasts are particularly well-suited for use in MFCs because they are harmless, widely available and robust under a broad range of conditions. Baker's yeast (*S. Cerevisiae*) is commonly used in the biofuels industry to convert six carbon sugars to alcohol through fermentation. Baker's yeast may be employed as an inexpensive and self-renewing MFC catalyst when used in combination with an electron mediator. However, attempts to use free floating or planktonic yeast cells in a solution in MFCs have necessarily involved a fairly low concentration of cells, yielding very low fuel cell power density. Formation of a biofilm on the fuel cell electrode would increase the number of yeast cells able to participate in power generation. And attempts to use biofilms having a higher concentration of cells to boost fuel cell power densities have been successful with other types of cells, such as Geobacter. However, in order to coax baker's yeast to form biofilms, it has generally been necessary to employ specialized experimental conditions and techniques such as nutrient starvation, or targeted genetic mutation.

Accordingly, there is a need for a high power density microbial fuel cell that can use baker's yeast as a catalyst. There is also a need for a method for preparation of a yeast biofilm that will significantly increase cell density adjacent an electrode, resulting in a higher power density microbial fuel cell. Such a method should be relatively uncomplicated and capable of practice in the field, under emergency conditions. There is also a need for a method for preparation of multiple yeast biofilms on the same anode to further increase the power density of the microbial fuel cell.

SUMMARY OF THE INVENTION

A yeast biofilm microbial fuel cell has anode and cathode chambers, each containing an electrolyte medium, with a proton conducting membrane positioned in communication between the chambers. A baker's yeast cell biofilm is adherent on the anode, which may comprise a plurality of electrodes. The baker's yeast is induced under electrical poising to form a biofilm on the electrode. A method of making the microbial fuel cell includes providing a fuel cell having an anode chamber with an anode in an initial anode electrolyte solution, a cathode chamber having a cathode in a cathode electrolyte solution, the chambers being separated by a proton conducting membrane, adding a quantity of baker's yeast and a quantity of a fuel source to the anode solution in the anode chamber, connecting a resistor across the anode and cathode to enable current flow through the resistor for a selected time interval to enable poising of the anode and formation of a yeast biofilm on the anode, replacing the anode solution with a fresh quantity of the initial anode solution, adding a selected quantity of fuel source to the replacement anode solution, and continuing to run the fuel cell for a selected time interval at a resistance of about 10,000 ohms. The steps of replacing the anode solution, adding fuel source and running the cell under load are repeated until the baker's yeast has formed a suitable biofilm on the anode.

Various objects and advantages of this microbial fuel cell and method will become apparent from the following description taken in conjunction with the accompanying drawings wherein are set forth, by way of illustration and example, certain embodiments of this yeast biofilm powered fuel cell.

The drawings constitute a part of this specification, include exemplary embodiments of the fuel cell and method, and illustrate various features thereof.

DETAILED DESCRIPTION

As required, detailed embodiments of the yeast biofilm catalyzed fuel cell are disclosed herein; however, it is to be understood that the disclosed embodiments are merely exemplary of the device, which may be embodied in various forms. Therefore, specific structural and functional details disclosed herein are not to be interpreted as limiting, but merely as a basis for the claims and as a representative basis for teaching one skilled in the art to variously employ the apparatus in virtually any appropriately detailed structure.

Figure 1:
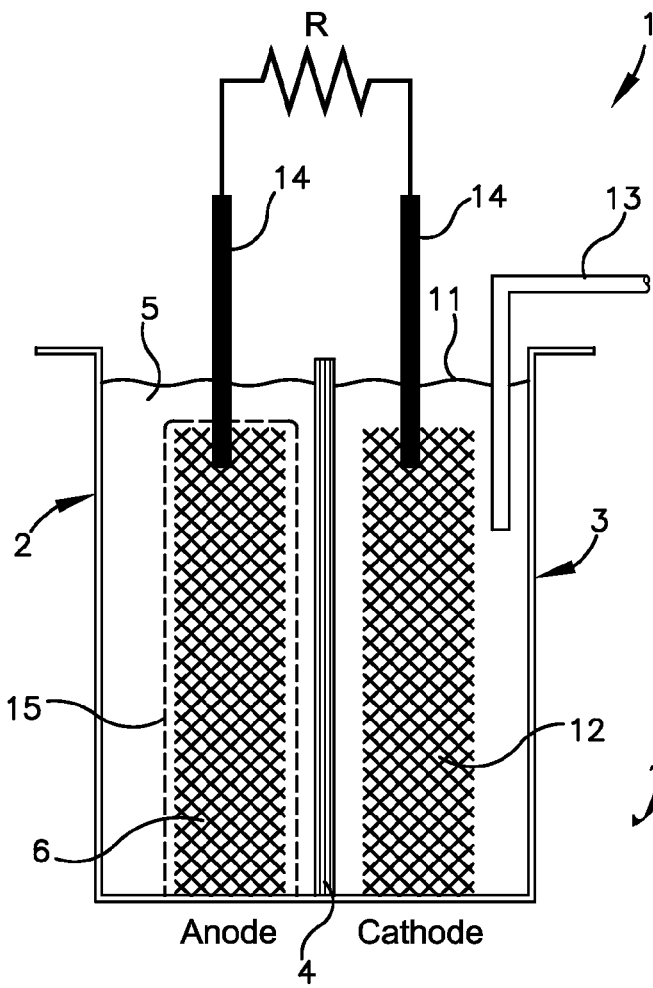
FIG. 1 is diagrammatic representation of a microbial fuel cell using a baker's yeast biofilm.

A baker's yeast catalyzed microbial fuel cell 1 is depicted in FIG. 1 to include an anode chamber or compartment 2 separated from a cathode chamber or compartment 3 by an ion exchange or proton conducting membrane 4, which allows protons produced in the anode chamber 2 to pass to the cathode chamber 3. The anode chamber 2 contains an anode solution 5 surrounding an anode component or anode 6. The anode 6 may be either a single structure as shown in FIG. 1, or it may include a plurality of anode structures or elements as exemplified in FIG. 4. The cathode chamber 3 contains a cathode solution 11 surrounding a cathode component or cathode 12. The cathode compartment 3 also includes an oxygen feed 13.

Any suitable proton conducting membrane 4 may be employed, with a perfluorosulfonic acid type membrane being particularly preferred. The anode 6 and cathode 12 electrodes may be constructed of any suitable material or combination of materials such as, for example, electrode quality carbon felt, carbon foam, stainless steel, nickel, gold, platinum or alloys or any other material that enables efficient transfer from the yeast cells to the electrode through electron mediation. Particularly preferred anodes 6 and cathodes 12 may be constructed of carbon felt or foam. It is foreseen that the anode 6 and cathode 12 need not be constructed of identical materials.

The initial anode solution 5 is an aqueous solution such as, for example, Minimal M9 broth or a medium including a quantity of an electron mediator such as, for example, methylionium chloride or Methylene blue, a ferricyanide, neutral red or gallocyanine, with Methylene blue preferred. The electron mediator has a concentration of from about 0.01 mM to about 60 mM/liter of anode solution, and a particularly preferred concentration of about 10 mM/liter. The anode solution 5 may also include from about 10 mM sodium chloride per liter of anode solution to about 3 M/liter, with a preferred concentration of about 100 m M/liter. The pH of the anode solution is from about 2.0 to about 11, with a preferred pH of about 7.0.

The initial cathode solution 11 is also an aqueous solution such as, for example, Minimal M9 broth or a medium including a quantity of an electron mediator such as, for example, a ferricyanide, with potassium ferricyanide being preferred. The electron mediator has a concentration of from about 10 mM/liter of cathode solution to about 200 mM/liter, with a particularly preferred concentration of about 50 mM/liter. Alternatively, a so-called air cathode may be employed, where the cathode is exposed to air, and catalyst particles embedded within the conductive cathodic matrix catalyze the reduction of oxygen in air to water. Such catalyst particles may include noble metals such as platinum and ruthenium and other transition metal-based catalysts such as iron phthalocyanine.

The anode 6 and cathode 12 are each connected to a conductor 14, such as copper wire or any other suitable electrically conductive path. The wires 14 are connected across a resistor R (FIG. 1), which may have a fixed value or it may be a variable resistor such as a potentiometer, rheostat, decade resistor or the like. The operating resistance may be from about 10 ohms to about 10,000 ohms, with about 5,000 ohms being preferred.

Figure 3:
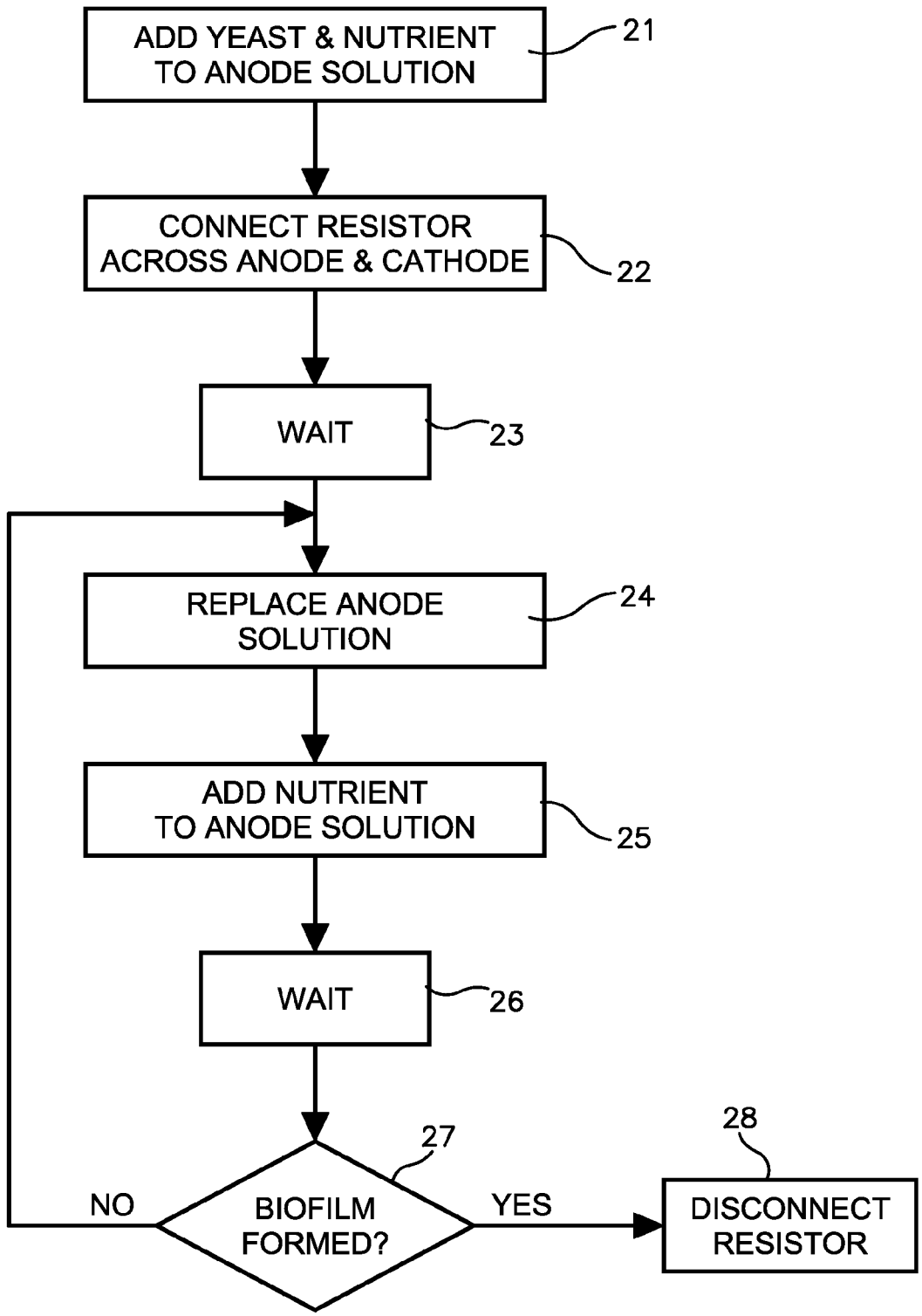
FIG. 3 is a flow diagram of a method of formation of yeast biofilm catalyzed fuel cells.
Figure 4:
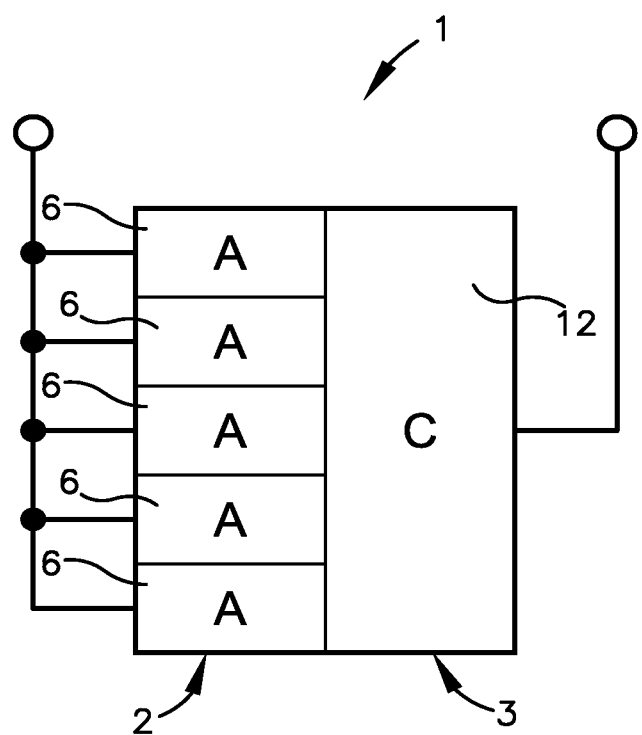
FIG. 4 is a diagrammatic representation of a biofilm fuel cell with multiple anodes.

An exemplary method of formation of yeast biofilm catalyzed fuel cells is depicted in FIG. 3. In this method baker's yeast and a yeast nutrient source or fuel source are added to the initial anode solution in the anode chamber of a conventional microbial fuel cell 1 and the cell is electrically poised by causing low level current to flow through resistance from the anode 6 to the cathode 12. The solution 5 in the anode chamber 2 is replaced periodically with a quantity of yeast-free initial anode solution to which a quantity of the nutrient source is added. No new yeast cells are added. Under such electrical poising of the fuel cell 1 with fairly high resistance (fairly low electrical current), the yeast cells are no longer required to give up all of their electrons to the electrode and are able to use some of the energy derived from catabolism of the fuel source to grow their biomass into a biofilm 15 of yeast cells that is adhered on or around the anode 6. Such greater yeast biomass results in greater fuel cell power density. A plurality of anodes 6 may be connected to provide a larger surface area and yield greater power density (FIG. 4). While FIG. 4 depicts an exemplary embodiment having five anodes, it is foreseen that any suitable number of anodes may be employed.

A fuel cell 1 is provided having an anode chamber 2 with an anode 6 in an initial anode solution 5, a cathode chamber 3 with a cathode 12 in an initial cathode solution 11 and a proton conducting membrane 4 between the chambers 2 and 3 (FIG. 1). A resistor R is connectable across the anode 3 and cathode 12 to enable conduction of an electrical current through a resistance of up to about 10,000 ohms.

As best shown in FIG. 3, in a first step (21) selected quantities of yeast and a fuel source such as a sugar are added to the initial anode solution 5 in the anode chamber 2. Baker's Yeast (*S. Cerevisiae*) is preferably employed and is added in a quantity of from about 0.1% to about 40% by weight or from about 0.001 mg/ml to about 500 mg/ml of the anode solution 5. While *S. Cerevisiae* is particularly preferred, it is foreseen that other yeast species may also be employed, either alone or in combination. The fuel source may be any type of sugar capable of being metabolized by yeast cells. The term "sugar" is intended to encompass those compounds commonly understood to be sugars, including monosaccharides, oligosaccharides and polysaccharides, the list of which is extensive and well-known by those skilled in the art. Particularly preferred fuel sources include glucose and other six carbon sugars such as fructose and galactose, and sucrose and other twelve carbon sugars such as lactose and maltose, or any combination thereof. However, any compound selected from the foregoing classes which is capable of metabolism by yeast cells could be used as a fuel source. It is foreseen that sucrose may be supplied in the form of a tree sap and that other sugars may be supplied in the form of any of a wide variety of animal and human food items, including those containing high fructose corn syrup.

The sugar may be added in a quantity of from about 0.1% to about 40% by weight of anode solution 5, with about 2% being particularly preferred. The resistor R is connected (22) across the anode 6 and the cathode 12 to enable current flow therethrough. The fuel cell 1 is run for a selected time interval (23) to enable poising of the anode 6 and formation of a biofilm 15 on the anode 6. The anode solution 5 is replaced (24) with a replacement quantity of the initial anode solution. A selected quantity of a fuel source is added (25) to the replacement anode solution 5, but no additional yeast is added. It is foreseen that the yeast nutrient or fuel source of the replacement anode solution need not be the same fuel source added to the initial anode solution or that it may comprise a solution including the fuel source added to the initial anode solution in combination with an additional fuel source or sources. The running of the fuel cell 1 is continued (26) for a selected time interval at a resistance of about 5,000 ohms. A user checks (27) the anode 6 to determine whether the yeast has formed a desired biofilm 15. If no suitable yeast biofilm 15 has formed, the anode solution is again replaced (24) and the subsequent steps are repeated until a suitable biofilm 15 is observed as shown in FIG. 1. A biofilm 15 may be visually observed after a period of time of from about 12 hours to more than about a week. The user then disconnects (28) the resistor R.

It is foreseen that the fuel cell 1 may be operated at a resistance of from about 10 ohms to about 10,000 ohms in one or both of the steps shown in box 22 and box 25. It is also foreseen that, as an alternative to forming the yeast cell biofilm 15 by operation of the fuel cell 1, the anode may be poised in a conventional three electrode configuration (not shown). The poising potential is dependent on the selection of the electron mediator. For Methylene blue, the poising potential may be from about −0.2 to about 0.8 volts with respect to the saturated calomel electrode.

Example Protocol

Microbial fuel cells (MFCs) were prepared for use in the subsequent examples in accordance with the following protocol:

Fleischmann's rapid rise baker's yeast (*S. Cerevisiae*) was resuscitated for 20 minutes in nutrient solution at temperatures of from 37-41° C. prior to each use. A 20 mg/ml solution based on dry yeast weight was used. A modified minimal M9 salts nutrient medium solution was prepared (1× M9 salts; 2 mM $MgSO_4$; 0.1 mM $CaCl_2$; 0.4% carbon source) using sterile water. A quantity of 2% dextrose (American Biosciences) was used as the sugar (carbon) source. A quantity of Methylene blue electron mediator in the chloride salt form (Sigma Aldrich) was made into 60 mM stock solutions by completely dissolving the salt in deionized water. Solutions with desired concentrations of electron mediator were prepared by adding appropriate amounts of the stock electron mediator solution to the M9 solution.

Microbial fuel cells were constructed using carbon felt as both the anode and cathode. These electrodes were separated by a Nafion® perfluorinated proton exchange membrane activated by boiling in saline solution for more than 1 hour. The nominal surface area of both electrodes was 6 $cm^2$. Both the anode and cathode chamber volumes were 10 ml. The anode compartment contained the yeast and 10 mM methylene blue in the nutrient solution while the cathode consisted of 50 mM potassium ferricyanide in the nutrient solution. Nitrogen was bubbled through the anode chamber and oxygen was bubbled through the cathode chamber. During film formation experiments the fuel cell was operated at a load of 5000 ohms. For power curve measurements, the fuel cell was operated under a variable resistor load, and at each load the current was allowed to stabilize for at least 5 minutes before a reading was taken.

After biofilm formation, the anodes were dried overnight under a ventilator hood. The masses of the attached biofilms were used to quantify the extent of biofilm formation using a mass balance. The dried biofilms were imaged using a scanning electron microscope (Philips), after sputter depositing a thin gold layer (Philips).

Example I

A conventional planktonic yeast microbial fuel cell (MFC) was prepared in accordance with the Example Protocol except that the M9 solution was used without addition of the electron mediator stock solution and the cell was not operated under 5000 ohm load in between the power readings.

Figure 2:
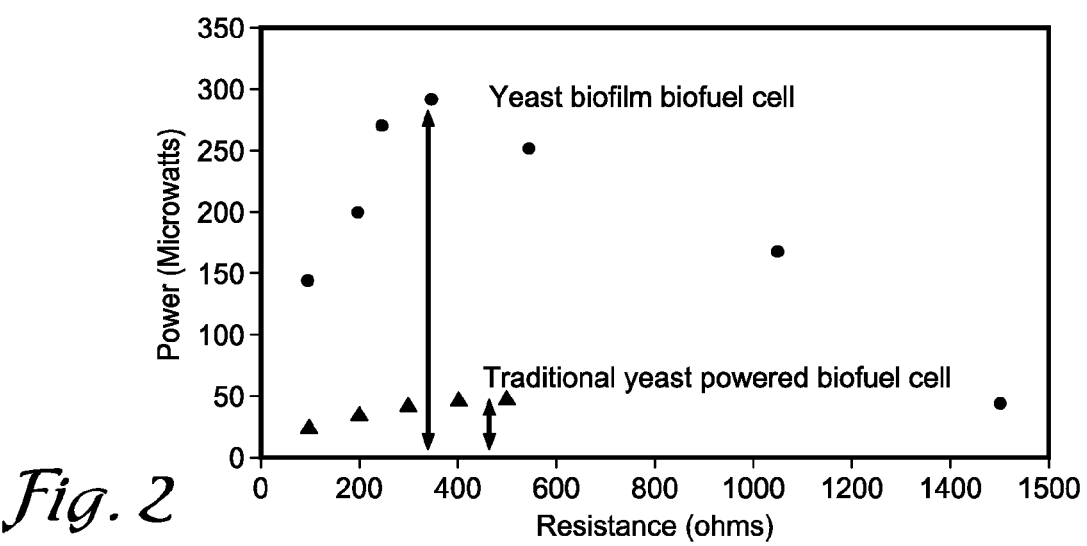
FIG. 2 is a graph showing the relationship of power to current in a microbial fuel cell using planktonic yeast compared with a microbial fuel cell using a yeast biofilm adjacent the anode.

The results of polarization measurements used to determine maximum power density of the planktonic yeast MFC are shown as the lower plot in FIG. 2. The power density was not observed to change, was observed to remain constant at about 25 $\mu W\ cm^{-2}$ and remained constant for a period of about 2 weeks.

Example II

A baker's yeast biofilm anode MFC was prepared as follows:

Yeast biofilms were formed on electrically biased anodes by first exposing the anodes to planktonic yeast suspension, and subsequently exposing the anodes with attached yeast cells to pure nutrient solution and an electron mediator. The first 3 days of preparation were identical to fabrication of the conventional planktonic yeast MFC described in the Example Protocol. However, subsequent to replacement of the solution in the anode chamber and the addition of pure nutrient solution containing no additional yeast, the anode solution was replaced with pure nutrient solution at the end of each day. The power density of the fuel cell was also measured at the end of each day. As shown in the upper plot in FIG. 2, the power density of the cell increased from about 10 $\mu W\ cm^{-2}$ at the end of day 3 to 50 $\mu W\ cm^{-2}$ (300 $\mu W$) at the end of day 6 during this time. No further increase of power density was observed with time. In conventional fuel cells, power densities may increase over a period of a few minutes, but subsequently remain constant. This 5-fold increase in power density is attributed to biofilm-like growth which was observed at the anode.

The anode was removed from the fuel cell and cut to half its size, and then subsequently cut to one-quarter of the original size. After each resizing, the power density was measured by replacing the anode in the anode compartment. Pure nutrient without additional yeast was added to the anode compartment and the power density was measured after a one hour period of equilibration. The power density measurements scaled with the surface area, which established that only the cells attached to the anode were contributing to the observed power generation. In addition to demonstrating surface area dependence on power, the anode resizing experiments also demonstrated that the anodes were robust against repeated exposure to the air.

Example III

Scanning electron micrographs from a conventional anode MFC prepared as in Example I and a biofilm anode MFC prepared as in Example II were compared to visually observe differences in microbe attachment to the respective anodes. Both anodes were processed for 6 days according to their respective protocols. The conventional anodes showed yeast cells trapped inside the fiber mesh of the felt anodes and virtually no build-up of cell mass. The measured cell masses on the conventional anodes were about 20 mg. The biofilm electrode showed a time-dependent build up of cell mass away from the anode. For anodes processed for 6 days and 14 days, the cell masses were respectively about 50 mg and about 100 mg. This suggests that biofilms continued to grow throughout the period of investigation, although the power densities showed no further increase after the first 6 days. Conformal coatings of cells were observed for the biofilm anode, but no such microstructure was observed for the conventional anode. It is postulated that the necessity for the absence of planktonic yeast in the replacement anode solution for the biofilm MFC is related to an increased need for availability of nutrients for the biofilm layer, especially for the cells embedded deeper within the layers. Although the yeast cell mass continuously increased during the period of investigation (14 days), the power density increase saturated after 6 days. This suggests the existence of other factors, such as mass transport limitations, that may serve to limit power density beyond the cell mass attached to the electrode.

Since the biofilm formation experiments involved growth of cell-attached electrodes in fresh nutrient solution with no additional added yeast cells, it was possible that the higher power densities that were observed were attributable to natural electrogenic microbes present in the nutrient solution. This possibility was investigated by the following Examples IV and V.

Example IV

Verification that the observed higher power densities were not attributable to natural electrogenic microbes present in the nutrient solution was performed as follows:

A biofilm anode formed over 6 days was removed from the anode solution, washed three times in a nutrient solution devoid of electron mediator, and was replaced in the anode chamber. Fresh nutrient solution devoid of electron mediator was added to the anode chamber and the polarization curve was measured after 1 hour. The measured power density declined from 50 μW cm$^{-2}$ to 12 μW cm$^{-2}$, suggesting that the power density observed for the MFC with biofilm anodes was enabled by electron mediators, and was not attributable to naturally electrogenic microbes.

Some electrogenic microbes are known to use naturally secreted soluble electron mediators to transfer electrons to the anode. It was possible that the washing step used to remove the artificial electron mediator methylene blue could have also removed such naturally produced mediators, resulting in the observed reduced power density. This possibility was investigated by the following Example V.

Example V

This experiment was designed to verify that any naturally produced electron mediators were not lost during the washing step used to remove the artificial electron mediator Methylene blue. The procedure of Example II for formation of a biofilm on the anode was performed, with the exception that an electron mediator was not used, either in the initial anode solution or thereafter in any replacement solution. The maximum observed power density was 2 μW cm$^{-2}$ after 1 day and the power density decreased continuously over the next 5 days. The cell mass attached to the felt microstructure of the anode was 20 mg, which was substantially less than the cell mass typically observed for biofilm anodes, suggesting that electrogenic microbes were not responsible for the power generation and the growth of such microbes was not a factor in the biofilm formation.

Taken together, the results of Examples IV and V establish that the increase in power density of the biofilm MFC of Example II is not attributable to naturally available electrogenic microbes. The reduced cell mass attached to the anode indicates that, beyond an initial attachment of cells, the further growth of cells attached to the anode requires enablement of the yeast cell mass to use the electrically poised anode as an electron acceptor.

Examples I-V show that electrical poising of an electrode leads to the growth of a thick layer of baker's yeast cells in the presence of an electron mediator. In large areas, yeasts were observed to be conformally coating electrode fibers. The biofilm layer of yeast resulted in high power density MFCs having power densities in excess of 50 μW cm$^{-2}$, which is more than two times the power density observed with comparable non-biofilm electrodes operated with planktonic yeast in solution. In the absence of an electron mediator, such biofilm growth was not observed, confirming that the yeast biofilm is formed by electrical poising or stimulation.

Advantageously, the conformal attachment of baker's yeast biofilms on and around anode fibers results from electrical poising of the electrode in the presence of electron mediators and the absence of planktonic yeast in solution. In addition to novel microstructure, the evidence for biofilm growth due to electrical poising is supported by the reduced cell mass which is observed where no electron mediator is added from the beginning. A significantly greater, time dependent cell mass was observed where the electron mediator methylene blue was employed. It is also possible to include multiple biofilm electrodes in the same anode chamber, to proportionally and significantly increase the volumetric power density of MFCs using the electrically-induced yeast biofilm layer.

It is to be understood that while certain forms of the yeast biofilm fuel cell and method thereof have been illustrated and described herein, it is not to be limited to the specific forms or arrangement of parts described and shown.

The following is claimed and desired to be secured by Letters Patent:

1. In a method of making a fuel cell having an anode chamber with an anode in a first anode solution, a cathode chamber having a cathode in an initial cathode solution, a proton conducting membrane therebetween, a resistor connectable across the anode and the cathode to enable conduction of current through a resistance of from 10 ohms to 10,000 ohms, the improvement comprising:

(a) adding a selected quantity of yeast cells and a selected quantity of a first yeast nutrient source to the first anode solution in the anode chamber;

(b) connecting the resistor across the anode and cathode to enable current flow therethrough for a selected time interval to thereby enable poising of the anode and formation of a yeast biofilm thereof on the anode;

(c) preparing a second anode solution different from said first anode solution;

(d) replacing the first anode solution with a replacement quantity of the second anode solution;

(e) adding a selected quantity of a second yeast nutrient source to said second anode solution where said second yeast nutrient source comprises either (i) a yeast nutrient source different than said first yeast nutrient source or (ii) a solution including said first nutrient source in combination with at least one different yeast nutrient source;

(f) continuing to run the fuel cell for the selected time interval at a resistance of from 10 ohms to 10,000 ohms; and (g) repeating steps (d) and (e) until the yeast has formed a desired biofilm on the anode.

2. A method of making a fuel cell as set forth in claim 1, wherein the anode and cathode are constructed to include a quantity of carbon felt.

3. A method of making a fuel cell as set forth in claim 1, wherein the anode comprises a plurality of electrodes.

4. A method of making a fuel cell as set forth in claim 1, wherein the first anode solution and the second anode solution each include a quantity of an electron mediator.

5. A method of making a fuel cell as set forth in claim 4, wherein the first anode solution and the second anode solution each include from 0.01 mM/liter to 60 mM/liter of Methylene blue.

6. A method of making a fuel cell as set forth in claim 4, wherein the first anode solution and the second anode solution each also include from 10 mM/liter to 3 M/liter of sodium chloride.

7. A method of making a fuel cell as set forth in claim 1, wherein the cathode solution includes a quantity of an electron mediator.

8. The method set forth in claim 7, wherein the cathode solution includes 50 mM/ml of potassium ferricyanide.

9. A method of making a fuel cell as set forth in claim 1, wherein the yeast comprises *S. cerevisiae*.

10. A method of making a fuel cell as set forth in claim 1, wherein the selected quantity of yeast added in step (a) comprises from 0.001 mg/ml to 500 mg/ml of anode solution.

11. A method of making a fuel cell as set forth in claim 1, wherein said first and second yeast nutrient source includes a sugar.

12. A method of making a fuel cell as set forth in claim 1, wherein the selected quantity of said first and second yeast nutrient source added in steps (a) and (e), respectively, comprise glucose in a concentration of from about 0.1% to about 40% by weight of anode solution.

13. A method of making a fuel cell as set forth in claim 1, wherein said first and second yeast nutrient source further comprises tree sap.

14. A method of making a fuel cell as set forth in claim 1, wherein the fuel cell is operated in steps (b) and (e) at a resistance of 5,000 ohms.

15. A method of making a fuel cell as set forth in claim 1, wherein the biofilm is formed by electrically biasing the electrode in a standard three electrode configuration at a potential of from about −0.2 volts to about 0.08 volts with respect to a saturated calomel electrode.

16. A method of making a fuel cell as set forth in claim 1, wherein the anode solution has a pH of from about 2.0 to about 11.0.

17. A microbial fuel cell comprising:
   (a) an anode chamber of two configurations, a first configuration having an anode in a first anode solution wherein said first anode solution includes a first yeast nutrient source;
   (b) a second configuration wherein said anode chamber has an anode in a second anode solution different from said first anode solution wherein said second yeast nutrient source comprises either (i) a yeast nutrient source different than said first yeast nutrient source or (ii) a solution including said first nutrient source in combination with at least one different yeast nutrient source;
   (c) a cathode chamber having a cathode in a cathode solution;
   (d) a proton conducting membrane positioned in communication between said anode chamber and said cathode chamber; and
   (e) said anode including a yeast cell biofilm adherent thereon.

18. A microbial fuel cell as set forth in claim 17, including a resistor connectable across said anode and said cathode to enable conduction of current through a resistance of from 10 ohms to 5,000 ohms.

19. A microbial fuel cell as set forth in claim 17, wherein said anode comprises a plurality of electrodes.

20. A microbial fuel cell as set forth in claim 17, wherein said first anode solution includes a quantity of an electron mediator.

21. A microbial fuel cell as set forth in claim 20, wherein said electron mediator comprises Methylene blue.

22. A microbial fuel cell as set forth in claim 17, wherein said cathode solution includes a quantity of an electron mediator.

23. A microbial fuel cell as set forth in claim 22, wherein said electron mediator comprises potassium ferricyanide.

24. A microbial fuel cell as set forth in claim 17, wherein said first anode solution includes a quantity of a yeast nutrient source.

25. A microbial fuel cell as set forth in claim 24, wherein said yeast nutrient source comprises tree sap.

26. A microbial fuel cell as set forth in claim 17, wherein said yeast cell biofilm comprises baker's yeast cells.

27. A microbial fuel cell including an anode component and a cathode component, comprising:
   (a) said anode component including an anode structure with a yeast biofilm Adherent thereon; and
   (b) said anode component of two configurations, a first configuration having a first anode solution and a second configuration having a second anode solution different from said first anode solution, a second configuration wherein said anode chamber has an anode in a second anode solution different from said first anode solution wherein said first nutrient source and second anode solution includes a second yeast nutrient source comprising either (i) a yeast nutrient source different than said first yeast nutrient source or (ii) a solution including said first nutrient source in combination with at least one different yeast nutrient source.

28. In the microbial fuel cell of claim 17 wherein said first anode solution contains a yeast nutrient source and said second anode solution does not contain yeast.

29. The microbial fuel cell of claim 17 wherein said second anode solution is free of yeast.

* * * * *